United States Patent
Wei et al.

(10) Patent No.: US 12,422,247 B2
(45) Date of Patent: Sep. 23, 2025

(54) CALIBRATION OF IMAGING SYSTEM WITH COMBINED OPTICAL COHERENCE TOMOGRAPHY AND VISUALIZATION MODULE

(71) Applicant: Alcon Inc., Fribourg (CH)

(72) Inventors: Wei Wei, Lake Forest, CA (US); Parisa Rabbani, Aliso Viejo, CA (US); Sahar Hosseinzadeh Kassani, Lake Forest, CA (US); Qiang Li, Irvine, CA (US); Lance Noller, Yorba Linda, CA (US)

(73) Assignee: Alcon Inc., Fribourg (CH)

( * ) Notice: Subject to any disclaimer, the term of this patent is extended or adjusted under 35 U.S.C. 154(b) by 189 days.

(21) Appl. No.: 18/354,096

(22) Filed: Jul. 18, 2023

(65) Prior Publication Data

US 2024/0027180 A1    Jan. 25, 2024

Related U.S. Application Data

(60) Provisional application No. 63/391,235, filed on Jul. 21, 2022.

(51) Int. Cl.
*G01B 9/02091* (2022.01)
*A61B 3/10* (2006.01)
(Continued)

(52) U.S. Cl.
CPC .......... *G01B 9/02072* (2013.04); *A61B 3/102* (2013.01); *A61B 90/20* (2016.02); *G01B 9/02091* (2013.01)

(58) Field of Classification Search
CPC ............ G01B 9/02072; G01B 9/02091; A61B 3/102; A61B 90/20; A61B 3/12; A61B 3/132; A61B 3/0025; G06T 5/50
See application file for complete search history.

(56) References Cited

U.S. PATENT DOCUMENTS

9,799,114 B2 * 10/2017 Piron ................ G09B 23/30
2010/0271498 A1 * 10/2010 Hwang ............... H04N 23/68
348/222.1
(Continued)

OTHER PUBLICATIONS

Klein, Stefan et al. "Elastix: a toolbox for intensity-based medical image registration." IEEE transactions on medical imaging, Jan. 2010, pp. 196-205, vol. 29, No. 1, IEEE.
(Continued)

*Primary Examiner* — Jonathan M Hansen
(74) *Attorney, Agent, or Firm* — Nayyer J. Siddiqi; Quinn IP Law

(57) ABSTRACT

An imaging system includes a housing assembly having a head unit configured to be at least partially directed towards a target site. An optical coherence tomography (OCT) module and a visualization module are located in the housing assembly and configured to respectively obtain OCT data and visualization data of the target site. The system includes a controller configured to generate a scanning pattern for a region of calibration selected in a calibration target. OCT data of the region of calibration is synchronously acquired. The controller is configured to obtain a projected two-dimensional OCT image of the region of calibration based on the OCT data, as an inverse mean-intensity projection. The controller is configured to register the projected two-dimensional OCT image to a corresponding view extracted from the visualization data, via a cascaded image registration process having a coarse registration stage and a fine registration stage.

19 Claims, 8 Drawing Sheets

(51) Int. Cl.
   *A61B 90/20*      (2016.01)
   *G01B 9/02055*    (2022.01)

(56) References Cited

U.S. PATENT DOCUMENTS

| | | |
|---|---|---|
| 2012/0249956 A1 | 10/2012 | Narasimha-Iyer et al. |
| 2015/0324966 A1* | 11/2015 | Clifton .................... G06T 7/337 |
| | | 382/128 |
| 2017/0007112 A1* | 1/2017 | Gonzalez .............. A61F 9/0084 |
| 2018/0168737 A1 | 6/2018 | Ren et al. |
| 2019/0059722 A1 | 2/2019 | Ono |
| 2021/0137634 A1* | 5/2021 | Lang ....................... A61B 90/00 |
| 2021/0169324 A1* | 6/2021 | Tripathi ............... H04N 13/246 |

OTHER PUBLICATIONS

Lowekamp, Bradley C. et al., "The Design of SimpleITK", Frontiers in Neuroinformatics, Dec. 2013, pp. 1-14, vol. 7, Article 45.
Shamonin, Denis P. et al., "Fast parallel image registration on CPU and GPU for diagnostic classification of Alzheimer's disease", Jan. 2014, pp. 1-15, vol. 7, Article 50.

\* cited by examiner

CALIBRATION OF IMAGING SYSTEM WITH COMBINED OPTICAL COHERENCE TOMOGRAPHY AND VISUALIZATION MODULE

CROSS REFERENCE TO RELATED APPLICATION

The present application claims the benefit of priority to U.S. Provisional Application No. 63/391,235 filed Jul. 21, 2022, which is hereby incorporated by reference in its entirety.

INTRODUCTION

The present disclosure relates to a calibration of an imaging system with a combined optical coherence tomography module and visualization module. Various imaging modalities are commonly employed throughout the world to image various parts of the human body. In some situations, the imaging modalities may be combined. For example, an optical coherence tomography (OCT) unit may be integrated with a visualization device (such as a camera) to provide improved guidance during surgery. To provide accurate, real-time and three-dimensional perceptional guidance in such an integrated system, the two imaging modalities should be aligned well. However, several challenges exist in aligning images from an OCT unit with other imaging modalities, including the complexity of mechanical scanning in point-scanning OCT systems. Additionally, manual calibration and semi-automatic calibration may be time-consuming and tedious. For example, manual calibration requires the use of experienced technical support staff to run the various step-by-step calibration procedures.

SUMMARY

Disclosed herein is an imaging system with a housing assembly having a head unit configured to be at least partially directed towards a target site. An optical coherence tomography (OCT) module and a visualization module are located in the housing assembly and configured to respectively obtain OCT data and visualization data of the target site. A controller is in communication with the OCT module and the visualization module. The controller has a processor and tangible, non-transitory memory on which instructions are recorded for a method of calibration.

The controller is configured to generate a scanning pattern for a region of calibration selected in a calibration target in a coordinate system of the visualization module, referred to as visualization space. OCT data of the region of calibration is synchronously acquired with the scanning pattern. The controller is configured to obtain a projected two-dimensional OCT image of the region of calibration based on the OCT data. The projected two-dimensional OCT image is an inverse mean-intensity projection on an en face viewing plane. The projected two-dimensional OCT image is overlaid with a corresponding view extracted from the visualization data. The controller is configured to register the projected two-dimensional OCT image to the corresponding view, via a cascaded image registration process having a coarse registration stage and a fine registration stage.

In one embodiment, the visualization module is a surgical microscope. The visualization module may be a stereoscopic camera, with the second set of data including first and second views of the target site. The target site may be an eye. Prior to registering the projected two-dimensional OCT image with the corresponding view extracted from the visualization data, the controller may be configured to perform automatic image resizing. The scanning pattern may be an orthogonal raster scanning pattern. A robotic arm may be operatively connected to and configured to selectively move the head unit. The robotic arm is selectively operable to extend a viewing range of the OCT module in three dimensions.

The controller may be adapted to calculate respective transformation parameters in the coarse registration stage based on a translation transformation matrix that compensates for mismatches in shift. In one embodiment, the controller is adapted to calculate respective transformation parameters in the fine registration stage based on an affine diffusion tensor image (DTI) registration, with the respective transformation parameters being based in part on a rotation matrix, a shear matrix and a scaling matrix.

The controller may be adapted to compensate for relatively small mismatches in shift introduced during operation of at least one of rotation, shear and scaling alignment. The rotation matrix may be expressed as $$\begin{bmatrix} \cos(\theta) & -\sin(\theta) \\ \sin(\theta) & \cos(\theta) \end{bmatrix},$$

where $\theta$ is the respective transformation parameter for rotation. The shear matrix may be expressed as $$\begin{bmatrix} 1 & Shx \\ Shy & 1 \end{bmatrix},$$

where Shx and Shy are shear parameters along a first transverse direction and a second transverse direction. The scaling matrix may be expressed as $$\begin{bmatrix} Cx & 0 \\ 0 & Cy \end{bmatrix},$$

where Cx and Cy are scaling parameters along a first transverse direction and a second transverse direction.

In one embodiment, controller is adapted to selectively execute a validation procedure, where the controller is adapted to select a region of interest in the visualization space and obtain respective voltages for OCT scanning based in part on the region of interest and respective transformation parameters. The validation procedure includes obtaining acquired OCT image based on the respective voltages and comparing the acquired OCT image with the region of interest. The region of interest may be a line in the visualization space that corresponds to a cross-sectional B-frame in OCT space. The region of interest may be a quadrilateral in the visualization space that corresponds to a three-dimensional volume in OCT space.

Disclosed herein is a method of calibrating an imaging system having a housing assembly and a controller with a processor and tangible, non-transitory memory. The method includes placing an optical coherence tomography (OCT) module and a visualization module in the housing assembly for respectively obtaining OCT data and visualization data of a target site. The head unit is at least partially directed towards the target site. The method includes generating a scanning pattern for a region of calibration selected in a calibration target in a coordinate system of the visualization module, referred to as visualization space. OCT data of the region of calibration is synchronously acquired with the scanning pattern.

The method includes obtaining a projected two-dimensional OCT image of the region of calibration based on the OCT data. The projected two-dimensional OCT image is an inverse mean-intensity projection on an en face viewing plane. The projected two-dimensional OCT image is overlaid with a corresponding view extracted from the visualization data. The method includes registering the projected two-dimensional OCT image to the corresponding view, via a cascaded image registration process having a coarse registration stage and a fine registration stage.

The above features and advantages and other features and advantages of the present disclosure are readily apparent from the following detailed description of the best modes for carrying out the disclosure when taken in connection with the accompanying drawings.

Figure 1:
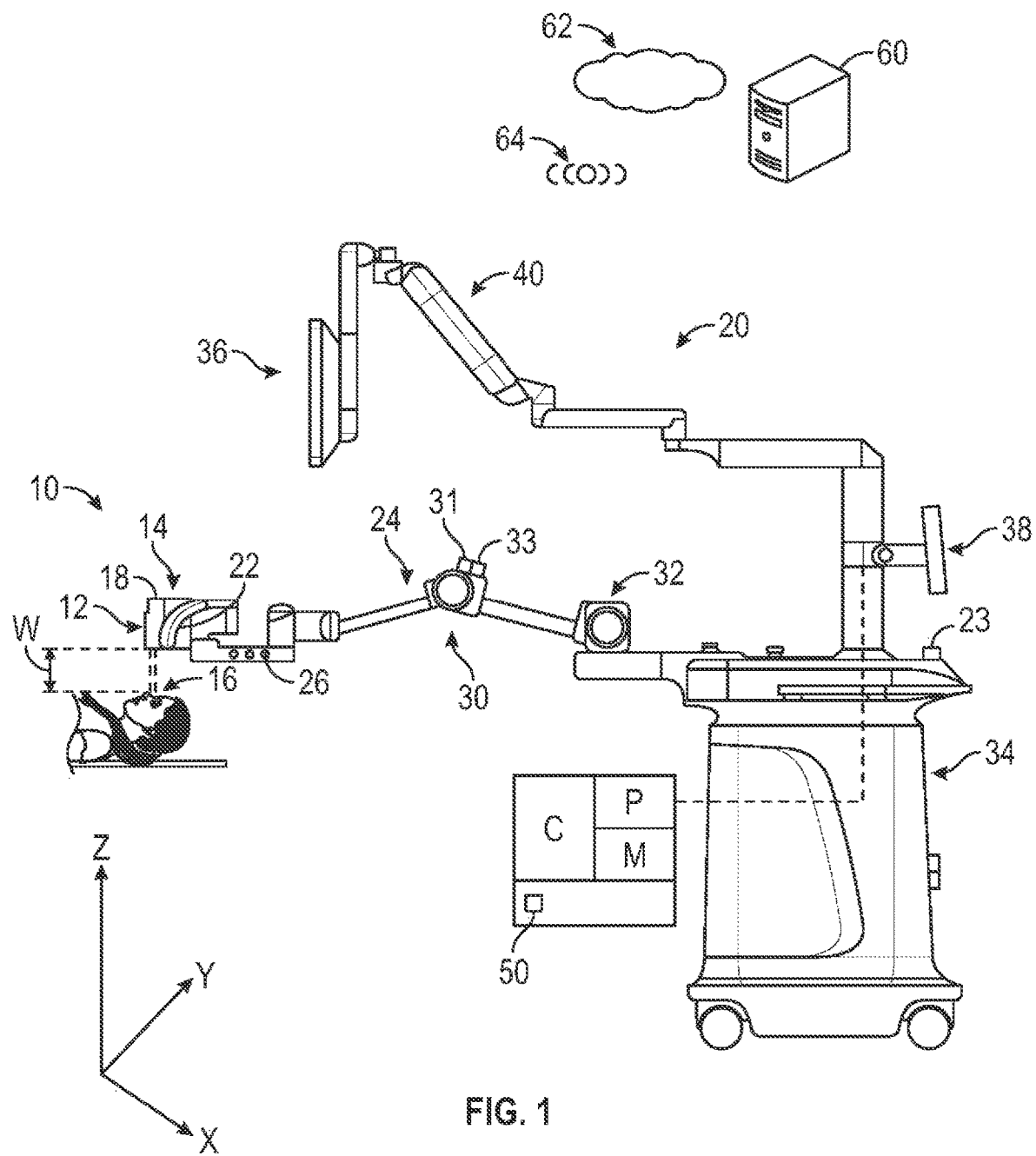
FIG. 1 is a schematic fragmentary perspective view of an imaging system having an optical coherence tomography (OCT) module, a visualization module and a controller.

Representative embodiments of this disclosure are shown by way of non-limiting example in the drawings and are described in additional detail below. It should be understood, however, that the novel aspects of this disclosure are not limited to the particular forms illustrated in the above-enumerated drawings. Rather, the disclosure is to cover modifications, equivalents, combinations, sub-combinations, permutations, groupings, and alternatives falling within the scope of this disclosure as encompassed, for instance, by the appended claims.

DETAILED DESCRIPTION

Referring to the drawings, wherein like reference numbers refer to like components, FIG. 1 schematically illustrates an imaging system 10 having a visualization module 12 and an optical coherence tomography module 14 (referred to hereinafter as "OCT module 14"). The imaging system 10 (referred to hereinafter as "system 10") is configured to image a target site 16. In some embodiments, the visualization module 12 is a stereoscopic camera configured to record first and second images of the target site 16, which may be employed to generate a live two-dimensional stereoscopic view of the target site 16. The visualization module 12 may be a digital surgical microscopic system integrated with the OCT module 14. In other embodiments, the visualization module 12 may be a single camera. It is understood that the system 10 may take many different forms and include multiple and/or alternate components and facilities.

Figure 8:
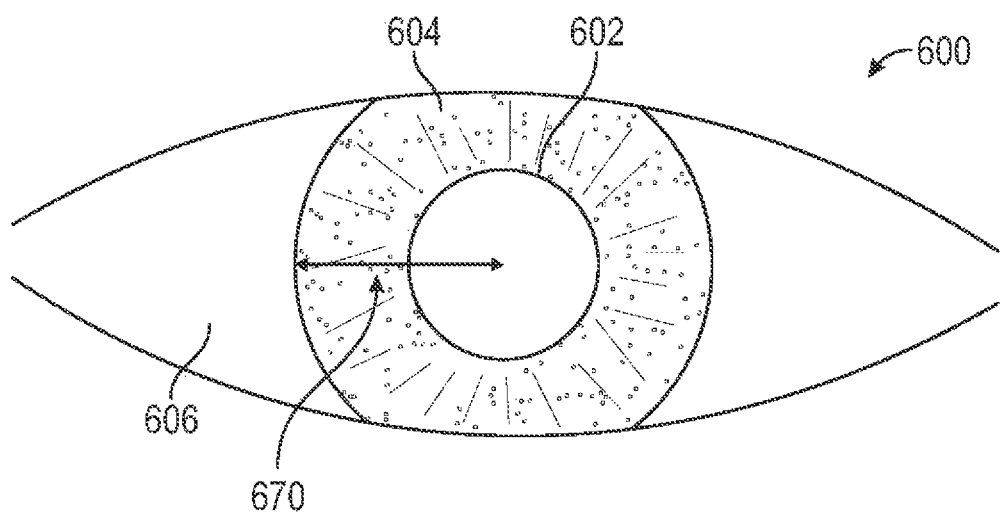
FIG. 8 is a is a schematic diagram of an example target site for the system of FIG. 1.

Referring to FIG. 1, the visualization module 12 may be located in a head unit 18 of a housing assembly 20, with the head unit 18 configured to be at least partially directed towards the target site 16. The target site 16 may be an anatomical location on a patient, a laboratory biological sample, calibration slides/templates, etc. In one example, referring to FIG. 8, the target site 16 is an eye 600 having a pupil 602, iris 604 and sclera 606.

The system 10 provides accurate OCT scanning at a targeted region of interest (such as region of interest 670 in FIG. 8) that is co-registered with the view from the visualization module 12, providing valuable information such as layered structure, tissue thickness, positions or sizes of incisions, stents, and intraocular lens etc. during ophthalmic surgery. As described below, a controller C in the system 10 is adapted to perform cascaded image registration and obtain a transformation matrix connecting respective spaces (i.e., coordinate systems) of the OCT module 14 and the visualization module 12.

Referring to FIG. 1, at least one input device 22 ("at least one" omitted henceforth) is operatively connected to the visualization module 12 (e.g., at the head unit 18) to allow a user to manually position it. The input device 22 may include respective controls for activating or selecting specific features, such as focus, magnification, adjusting an amount/type of light projected onto the target site 16 and other features. It is understood that the number and form of the input devices 22 may be varied, for example, the input device 22 may include a joystick, wheel, mouse or touchscreen device. In some embodiments, the input device 22 may be controlled via a remote-control unit 23 (see FIG. 1).

In some embodiments, the system 10 may include a robotic arm 24 operatively connected to and configured to selectively move the head unit 18. For example, referring to FIG. 1, the robotic arm 24 may be selectively operable to extend a viewing range of the OCT module 14 along an X-direction, Y-direction and Z direction. Referring to FIG. 1, the head unit 18 may be mechanically coupled to the robotic arm 24 via a coupling plate 26. The robotic arm 24 may include one or more joints, such as first joint 30 and second joint 32, configured to provide further degrees of positioning and/or orientation of the head unit 18. Referring to FIG. 1, a respective joint motor (such as joint motor 31) and a respective joint sensor (such as joint sensor 33), may be coupled to each joint. The joint motor 31 is configured to rotate the first joint 30 around an axis, while the joint sensor 33 is configured to transmit the position (in 3D space) of the first joint 30.

The head unit 18 may be connected to a cart 34 having at least one display medium (which may be monitor, terminal or other form of two-dimensional visualization), such as first and second displays 36 and 38 shown in FIG. 1. The housing assembly 20 may be self-contained and movable between various locations. Returning to FIG. 1, the first display 36 may be connected to the cart 34 via a flexible mechanical arm 40 with one or more joints to enable flexible positioning. The flexible mechanical arm 40 may be configured to be sufficiently long to extend over a patient during surgery to provide relatively close viewing for a surgeon. The first and second displays 36 and 38 may include any type of display including a high-definition television, an ultra-high-definition television, smart-eyewear, projectors, one or more computer screens, laptop computers, tablet computers, and/or smartphones and may include a touchscreen.

Referring to FIG. 1, the system 10 includes a controller C having at least one processor P and at least one memory M (or non-transitory, tangible computer readable storage medium) on which instructions are recorded for executing method 400, described below with respect to FIG. 5, of operating a calibration mode 50. The memory M can store controller-executable instruction sets, and the processor P can execute the controller-executable instruction sets stored in the memory M. The OCT module 14 and the visualization module 12 may include integrated processors in communication with the controller C.

Referring to FIG. 1, the controller C may be configured to process signals for broadcasting on the first and second displays 36 and 38. The first and second displays 36 and 38 may incorporate a stereoscopic display system, with a two-dimensional display having separate images for the left and right eye respectively. To view the stereoscopic display, a user may wear special glasses that work in conjunction with the first and second displays 36, 38 to show the left view to the user's left eye and the right view to the user's right eye.

The visualization module 12 is configured to acquire images of the target site 16, which may be presented in different forms, including but not limited to, captured still images, real-time images and/or digital video signals. "Real-time" as used herein generally refers to the updating of information at the same rate as data is received. More specifically, "real-time" means that the image data is acquired, processed, and transmitted at a high enough data rate and a low enough delay that when the data is displayed, objects move smoothly without user-noticeable judder or latency. Typically, this occurs when new images are acquired, processed, and transmitted at a rate of at least about 30 frames per second (fps) and displayed at about 60 fps and when the combined processing of the video signal has no more than about $\frac{1}{30}^{th}$ second of delay.

The system 10 calibrates the respective spaces or coordinate systems of the two imaging modalities (the OCT coordinate space and the visualization coordinate space) from the perspective of acquired images (i.e., end-to-end calibration). This covers mismatches from multiple sources, including mechanical scanning, the imaging optics and mismatching due to the surgical environment. The processing algorithm in the calibration is much faster than that through simulation of two-dimensional Galvo movement, manual calibration or semi-automatic calibration.

The system 10 does not require accurate image segmentation, which reduces the burden for additional image processing. As described below, the use of the method 400 for OCT calibration at a specific working distance W (see FIG. 1) and/or with a certain zoom ratio may be automated to function with a one-click of a button, in which all the data acquisition, post-processing and matrix calculation are accomplished by the controller C. Where the visualization module 12 and OCT module 14 work with various zoom ratios, a list of repeated calibrations at multiple depths may be performed and stored in a look up table.

Figure 7B:
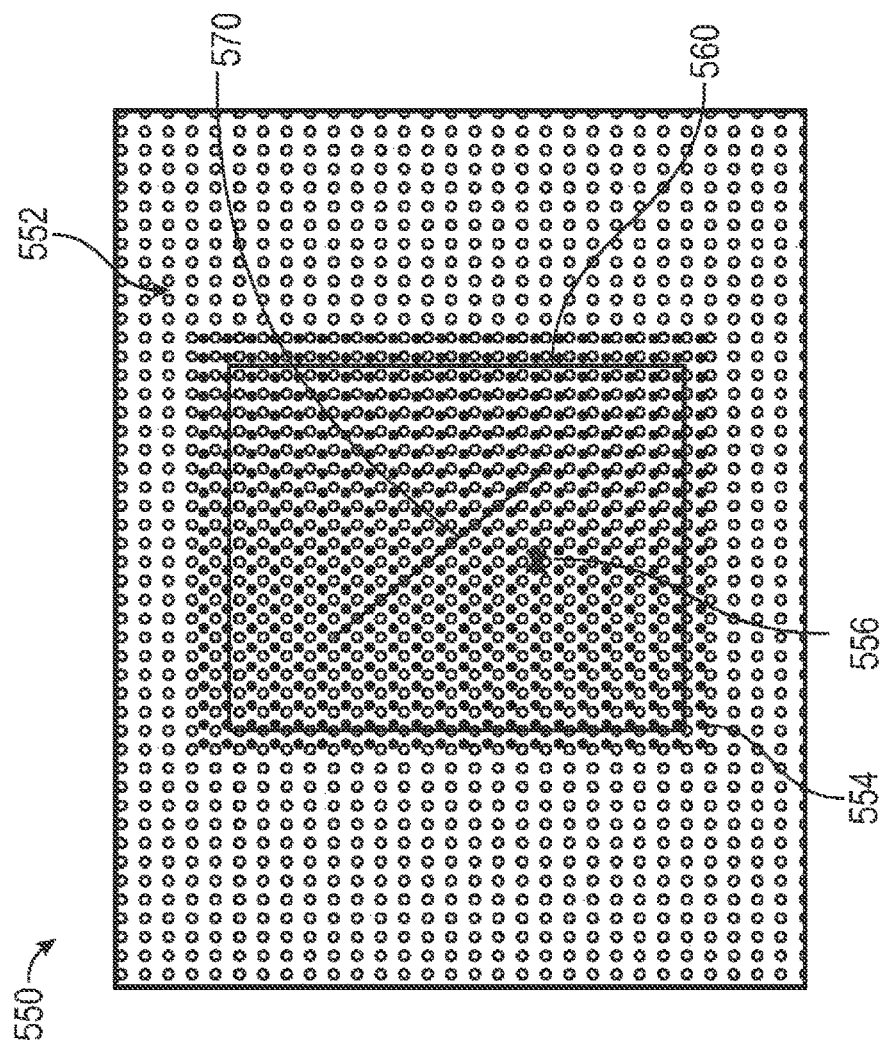
FIG. 7B is a schematic diagram of a captured image of the calibration target of FIG. 7A.
Figure 7A:
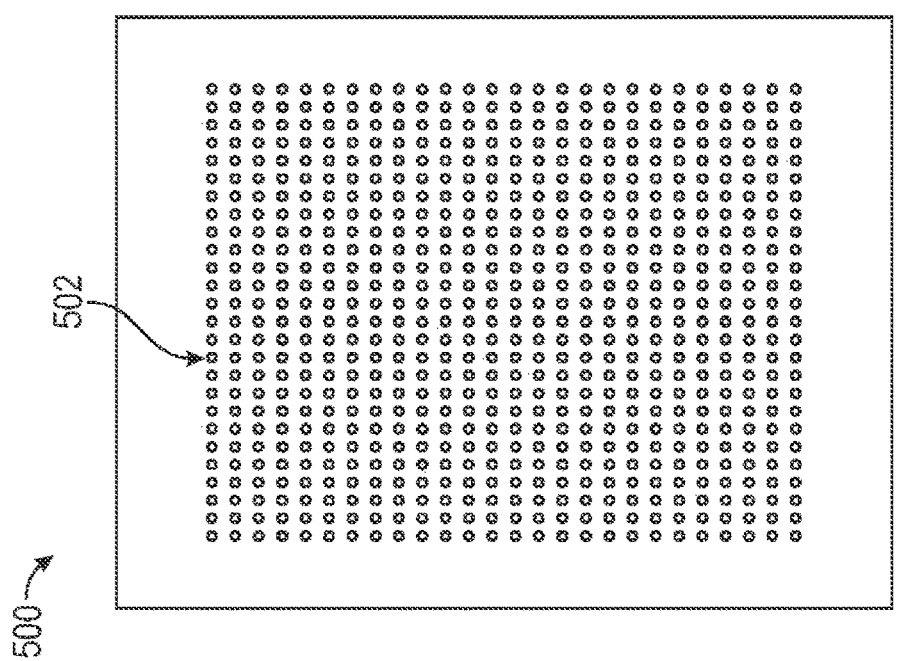
FIG. 7A is a schematic diagram of an example calibration target employable by the system of FIG. 1.

The system 10 employs a cascaded intensity-based multimodal image registration through a step-by-step auto resizing and translation registration of images acquired from a calibration device (e.g., calibration target 500 shown in FIG. 7A). Registration may be understood as the alignment in rotation, translation, and scale of the view(s) of the visualization module 12 to the view(s) of the OCT module 14, as well as matching the respective perspectives. The controller C is adapted to employ the calibration parameters to overlay the OCT cross-sectional B-scans with the corresponding en-face view regions in the image obtained by the visualization space (i.e., the validation of calibration).

The system 10 may employ an affine diffusion tensor for the image registration. After image registration, the calibration parameters (e.g., rotation, shear, scaling, and shift parameters) are generalized as an affine matrix in a homogeneous coordinate space, which can be further used to convert any region of interest in the visualization space (e.g., camera space) to a well-registered pattern of OCT scanning. This allows the depth-resolved cross-section (that has been registered) of a target site 16 to be synchronously displayed. Affine transformation is a linear mapping method that preserves points, straight lines, and planes.

Figure 2:
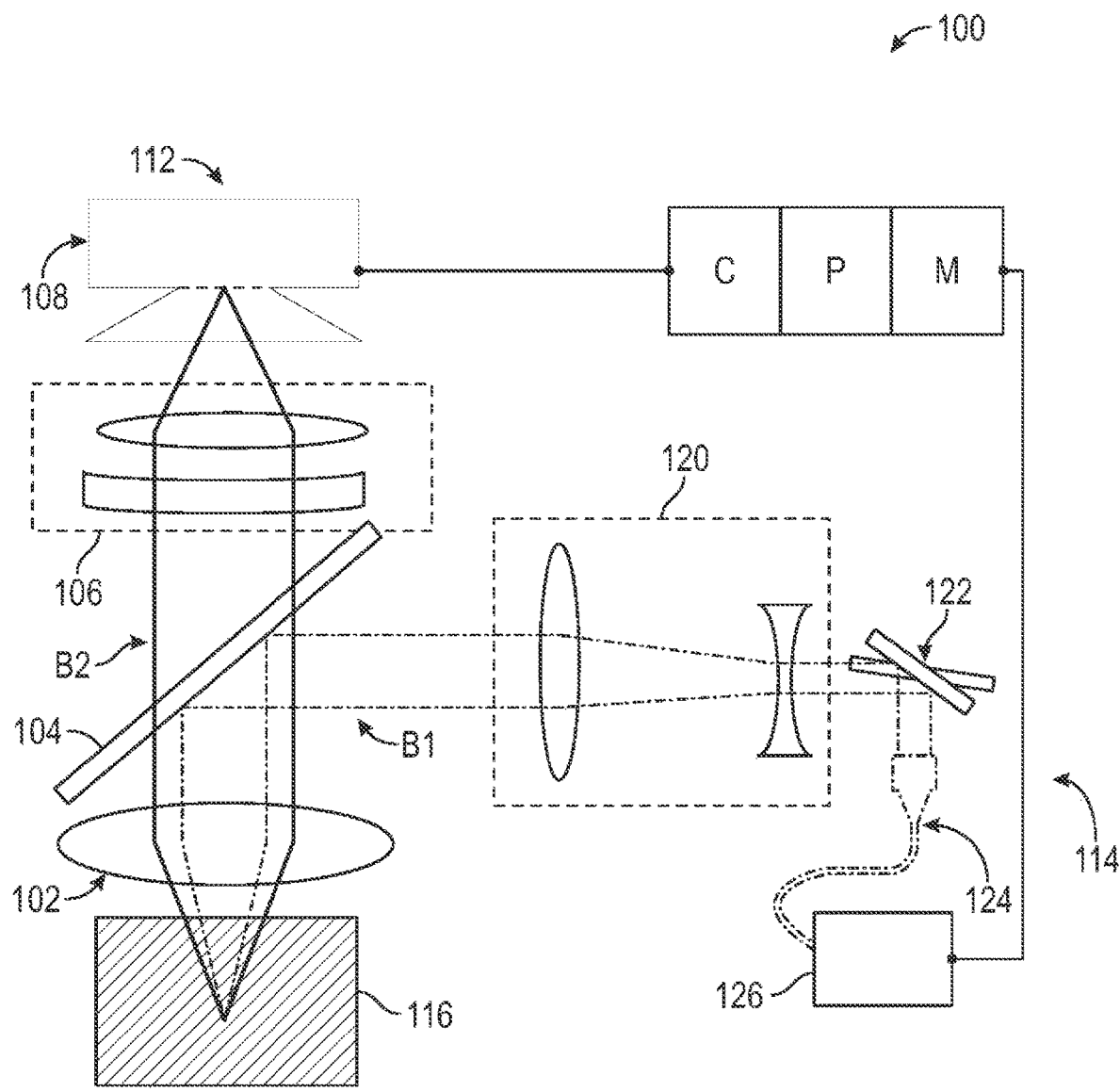
FIG. 2 is a schematic diagram of a portion of the system of FIG. 1, in accordance with a first embodiment.

Referring now to FIG. 2, a portion of the system 10 is shown, in accordance with a first embodiment. The apparatus 100 of FIG. 2 includes an exemplary visualization module 112 that is integrated with an OCT module 114 through a shared objective lens 102. The apparatus 100 includes a dichroic mirror 104. The visualization module 112 may include a dichroic mirror 104, a set of magnifying/focusing optics 106, and a high-resolution two-dimensional camera 108 for imaging a target site 116.

Referring to FIG. 2, the OCT module 114 includes beam expander optics 120, a two-dimensional scanner 122, a collimator 124, and an OCT engine 126. The two-dimensional scanner 122 may be a XY Galvo scanner set, a resonant scanner set, micro-electromechanical systems (MEMS) scanners, or other scanners that can perform raster, orthogonal or equivalent two-dimensional beam scanning. Galvo scanners, also called Galvanometer optical scanners, include motorized mirror mounts for laser-beam steering or scanning applications. The OCT engine 126 may be a spectral domain OCT, a swept source OCT, or a time domain OCT that utilizes light point-scanning or point-detection technology.

Referring to FIG. 2, the target site 116 is laterally scanned by a first beam B1 originating in the OCT module 14. The scanned region of first beam B1 at least partially overlaps with a second imaging path B2 (separately illuminated by a light source and imaged by a camera in the visualization module 112) at the target site 116. Fiber optics may be employed to transport and/or guide the first beam B1 and direct it to fall in the form of a spot scan onto an appropriate region of interest in the target site 116. The apparatus 100 may include any suitable additional optical or mechanical components for manipulating the light beams and automating the adjustment available to those skilled in the art. The scanned OCT dataset (which may be three or two-dimensional) and the images of the target site 116 may be sent to the controller C.

Figure 3:
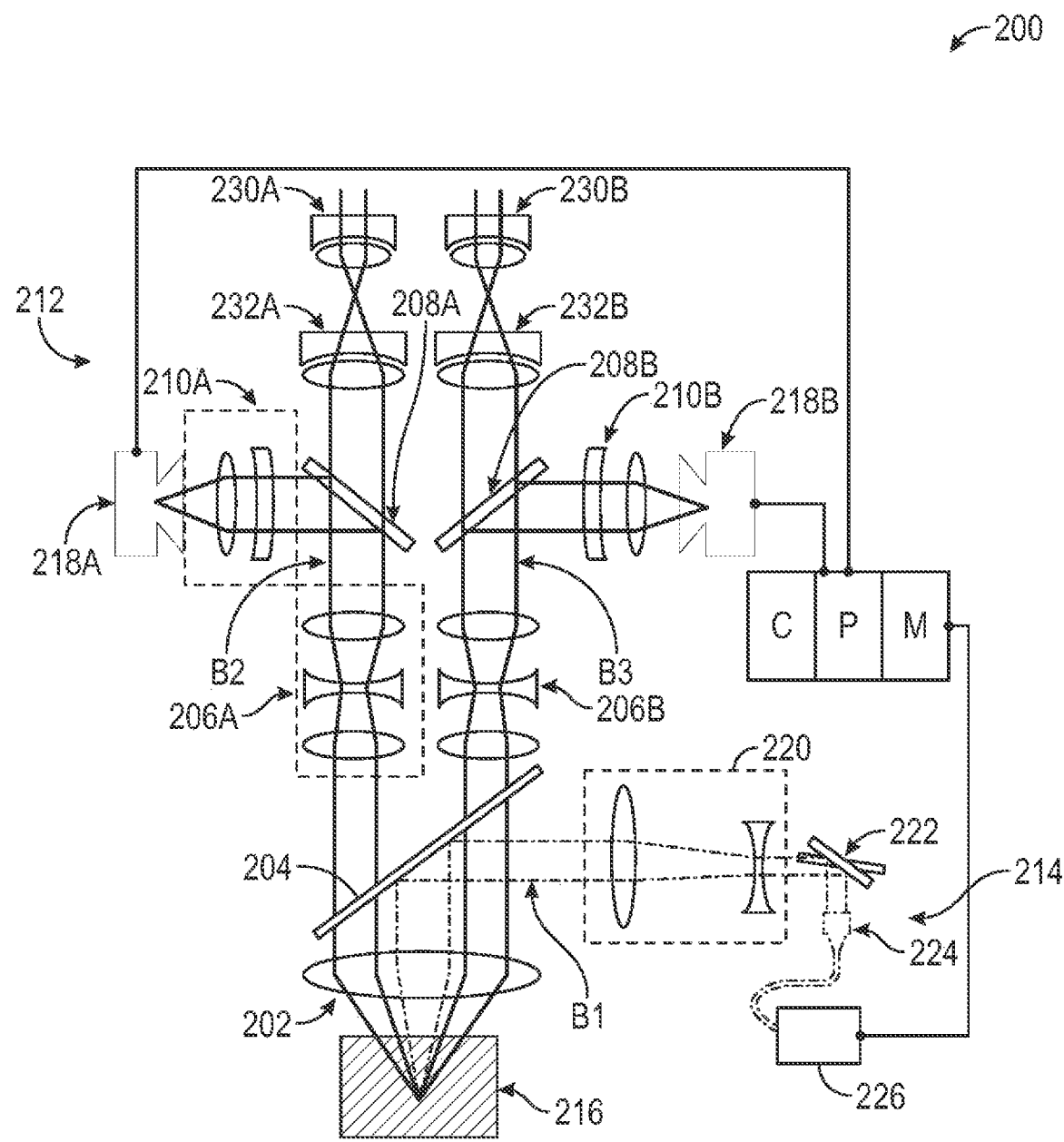
FIG. 3 is a schematic diagram of a portion of the system of FIG. 1, in accordance with a second embodiment.

Referring now to FIG. 3, a portion of the system 10 is shown, in accordance with a second embodiment. The apparatus 200 of FIG. 3 includes an exemplary visualization module 212 that is integrated with an OCT module 214 through a shared objective lens 202. The apparatus 200 includes a dichroic mirror 204. Referring to FIG. 3, the visualization module 212 includes two zooming optics sets 206A, 206B (for beams B2 and B3, respectively), two beam splitters 208A, 208B, two sets of magnifying/focusing optics 210A, 210B, and two high-resolution two-dimensional cameras 218A, 218B for imaging a target site 216.

In this embodiment, the visualization module 212 is a binocular surgical microscope. Referring to FIG. 3, the visualization module 212 includes two eye pieces 230A, 230B respectively connected to tube lens sets 232A, 232B. The images from the dual cameras 218A, 218B may be combined as a heads-up 3D visualization system by transmitting images to the first and second displays 36, 38 (see FIG. 1). This allows ophthalmic surgeons to alternatively replace surgical microscope eyepieces with high-resolution stereoscopic cameras. As shown in FIG. 3, the OCT module 214 may include beam expander optics 220 (for beam B1), two-dimensional scanners 222, a collimator 224, and an OCT engine 226.

Figure 4A:
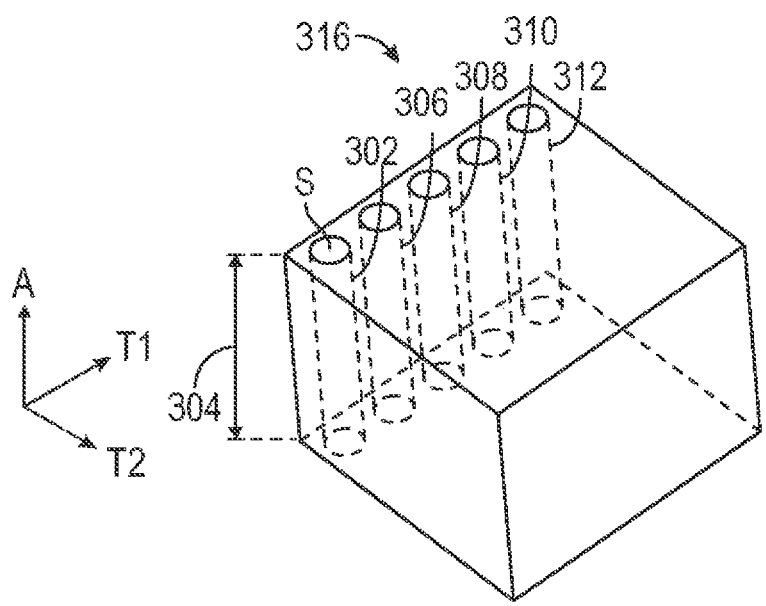
FIGS. 4A and 4B are schematic fragmentary perspective views of example scanning regions for the OCT module of FIG. 1.
Figure 4B:
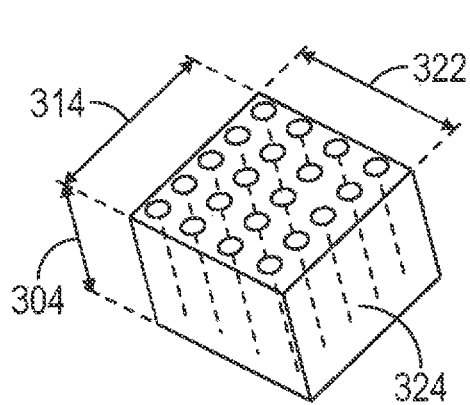
Figure 4C:
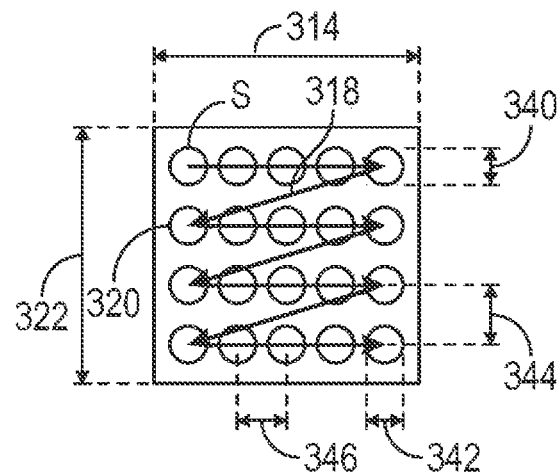
FIG. 4C is a schematic fragmentary top view of an example scanning pattern for the OCT module of FIG. 1.

Example scanning regions that may be utilized for the OCT module 114, 214 are shown on FIGS. 4A-C. It is understood that the views shown in FIGS. 4A-C are intended as non-limiting examples. FIGS. 4A and 4B are schematic fragmentary perspective views while FIG. 4C is a schematic fragmentary top view of an example scanning pattern. Referring to FIG. 4A, a single scan directed at a spot scan S (of the target site 116, 216) results in a depth scan 302 of the structure of the physical sample into which a beam (e.g., beam B1) originating from the OCT module 114, 214 is directed, along the incident direction. Referring to FIG. 4A, the depth scan 302 may be referred to as an "A-scan" and is configured to scan to a detected depth 304 along an axial direction A.

Referring to FIG. 4A, the beam B1 of FIGS. 2-3 may be moved in a continual manner about the target site 116, 216 to enable a second depth scan 306, a third depth scan 308, a fourth depth scan 310 and a fifth depth scan 312 along a first transverse scan range 314. Such a line of A-scans may be referred to as a B-scan or row scan 316. Referring to FIG. 4C, a grid of depth scans may be traced out along the first transverse scan range 314 and a second transverse scan range 322, by steering the optical path appropriately along the first transverse scan range 314, then performing a "step-and-repeat" path steer along a raster pattern 318 to repeat the cycle at a starting point 320 and subsequent lines. Referring to FIG. 4B, this results in a three-dimensional sampled volume 324, which may have the shape of a cuboid.

The movement of the beam B1 along with the processing of each A-scan (e.g., second depth scan 306, a third depth scan 308, a fourth depth scan 310 and a fifth depth scan 312) may be synchronized with the rest of the system 10 by the controller C and/or the OCT engine 126, 226, such that the downstream processes may reassemble the scans in the same order and relative location during the reconstruction process.

Referring to FIG. 4C, the diameter of the spot scan S may be represented by a first set of dimensions 340 and 342. In one example, the first set of dimensions 340 and 342 are equal and in the range of approximately 15 μm to 80 μm. In other examples, they are not equal. Referring to FIG. 4C, the separation of adjacent ones of the A-scans or depth scans 302 may be represented by a second set of dimensions 344 and 346.

Figure 5:
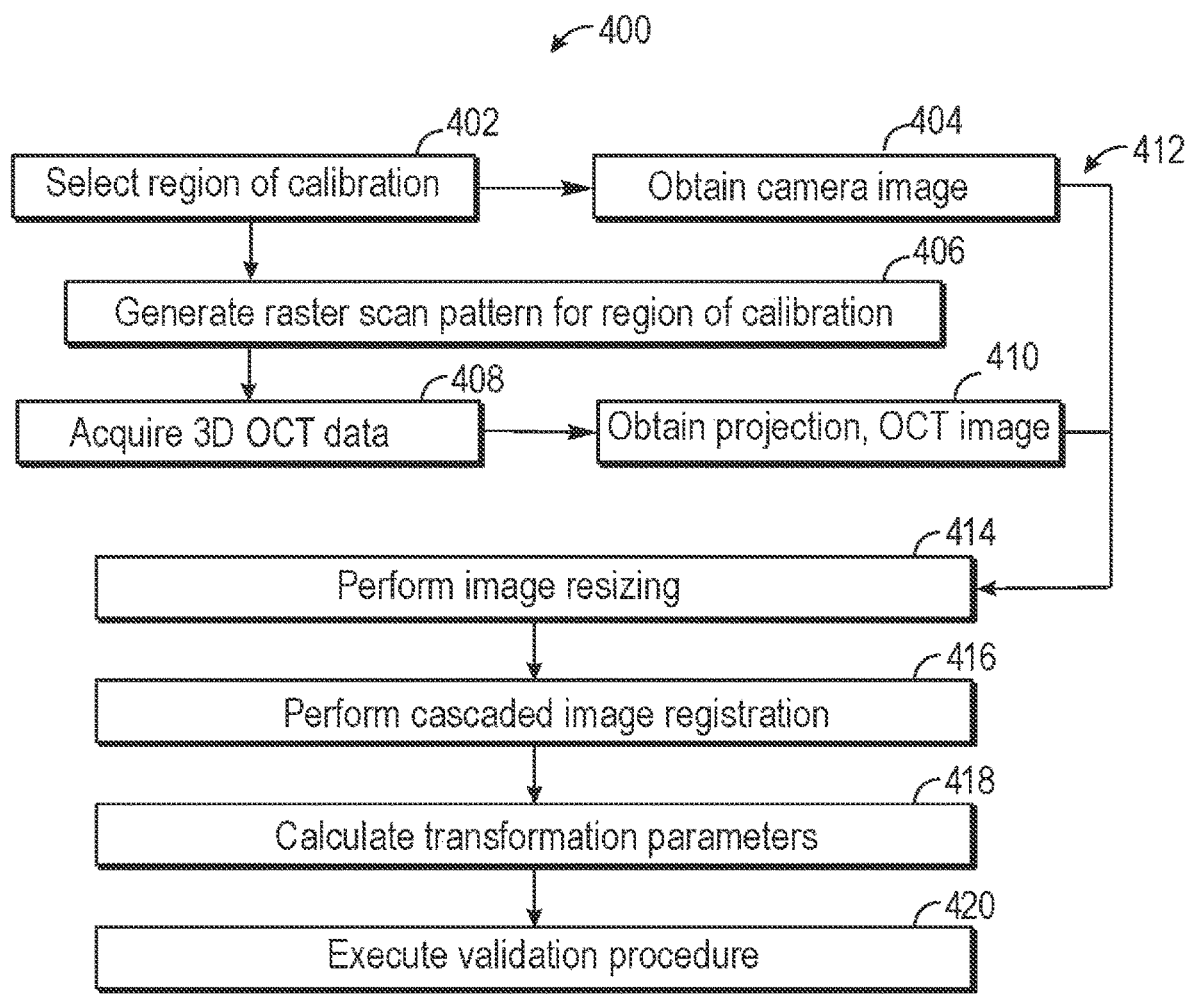
FIG. 5 is a flowchart of an example method executable by the controller of FIG. 1.

Referring now to FIG. 5, a flowchart is shown of an example method 400 for operating the calibration mode 50 of FIG. 1. Method 400 may be embodied as computer-readable code or instructions stored on and partially executable by the controller C of FIG. 1. Method 400 need not be applied in the specific order recited herein and may be dynamically executed. Furthermore, it is to be understood that some steps may be eliminated. Method 400 may be executed periodically or at predefined time intervals.

Per block 402 of FIG. 5, the controller C is programmed to select a region of calibration (ROC) for a calibration target in the visualization space (e.g., camera coordinate space). FIG. 7A shows an example calibration target 500 employable by the system 10. The calibration target 500 may be a low-reflective or high-reflective gridded-dot distortion target. The calibration target 500 may include a plurality of dots 502 of various sizes, arranged in a regular fixed frequency grid. In one embodiment, the calibration target 500 is a 3"×3" low-reflective gridded-dot distortion target with dot size of 0.25 mm. FIG. 7B is a schematic diagram of a captured image 550 of the calibration target 500, showing an example region of calibration 560.

From block 402, the method 400 advances to block 404 and block 406. Per block 404, a respective image (e.g., captured image 550 in FIG. 7B) from the visualization module 12 that covers the region of calibration 560 is captured and streamed into the controller C. Per block 406, the method 400 includes generating a scanning pattern for the region of calibration 560 selected in the calibration target 500. The scanning pattern may be a raster orthogonal scanning pattern, according to the Galvo domain field of view of the region of calibration 560. In raster scanning, a beam may sweep horizontally from a first end to a second end at a steady rate, then blank and rapidly move back to the first end, where it turns back on and sweeps out the next line. During this time, the vertical position is steadily increasing at a slower rate, with one vertical sweep per image frame and one horizontal sweep per line of resolution.

Proceeding to block 408 of FIG. 5, synchronous with the scanning, the controller C is programmed to acquire OCT raw data of the scanned region. The two or three-dimensional scanned OCT dataset and the respective images of the calibration target 500 from the visualization module 12 may be sent to the controller C. The scanned OCT dataset may be 3D volumes or two-dimensional B-frames that includes sequentially scanned A-scans (depth scans), according to various scanning patterns.

Advancing from block 408 to block 410 of FIG. 5, the raw OCT data is post-processed through an OCT reconstruction pipeline including background removal, spectral windowing, dispersion compensation, fast Fourier transform and logarithmic compression, into a depth-resolved 3D volume. While some processing techniques are described above, it is understood that other techniques may be employed. The 3D OCT volume is further processed through an inverse mean-intensity projection onto an en face view plane, as a projected view or OCT image in the X-Y plane (see FIG. 1). An en face view plane may be defined as having the face or front facing forward. FIG. 7B shows an example overlayed en face view display. The projected two-dimensional OCT image (represented by the second set of dots 554 in FIG. 7B) is overlaid with a corresponding view extracted from the visualization data (represented by the first set of dots 552).

The method 400 advances to block 414 from block 404 and block 410, as indicated by line 412. Per block 414 of FIG. 5, the controller C may be programmed to perform automatic image resizing. As the two images are from different imaging modalities with different pixel sizes and different sample numbers, an automatic image resizing may be desired to place two images into the same graphic user interface (GUI) widget, based on the horizontal and vertical peak counting of the repeated pattern (e.g., dot pattern in the calibration target 500 shown in FIG. 7A) being imaged.

Advancing to block 416 of FIG. 5, the method 400 includes finding detailed correlations or transformations between the respective spaces (or coordinate systems) of the visualization module 12 and the OCT module 14 through a cascaded image registration process. In the embodiment shown, the respective images from the visualization module 12 may be regarded as fixed images while the respective images from the OCT module 14 may be regarded as moving images to be registered with the fixed images.

As noted above, the first set of dots 552 (not shaded) in FIG. 7B represent the respective image of the calibration target 500 in visualization space while the second set of dots 554 (shaded) represent the inversed mean-intensity projection of a raster-scanned OCT volume. In the example shown in FIG. 7B, there is a mismatch between the first set of dots 552 and the second set of dots 554 that will be corrected by the cascaded image registration process in block 416.

The cascaded image registration process has a coarse registration stage and a fine registration stage. The coarse registration stage is based on a translation transformation matrix that corrects relatively large mismatches in shift. The fine registration stage is based on an affine diffusion tensor image (DTI) registration that handles mismatches in rotation, shear, and scaling, The transformation matrix may be represented as:

$$\begin{bmatrix} A11 & A12 & A13 \\ A21 & A22 & A23 \\ 0 & 0 & 1 \end{bmatrix}. \quad \text{(eq. 1)}$$

The controller C is adapted to compensate for a relatively small shift that may be introduced during the changing of the first three deformations (rotation, shear, and scaling). Considering the relatively small shift separately, the affine matrix may be represented as:

$$\begin{bmatrix} A11 & A12 \\ A21 & A22 \end{bmatrix}.$$

The affine matrix is a product of a rotation matrix, a shear matrix and a scaling matrix. The rotation matrix may be represented as $$\begin{bmatrix} \cos(\theta) & -\sin(\theta) \\ \sin(\theta) & \cos(\theta) \end{bmatrix}.$$

the shear matrix may be represented as $$\begin{bmatrix} 1 & Shx \\ Shy & 1 \end{bmatrix}$$

and the scaling matrix may be represented as $$\begin{bmatrix} Cx & 0 \\ 0 & Cy \end{bmatrix}.$$

Here θ is the respective transformation parameter for rotation while Shx, Shy and Cx, Cy are shear parameters and scaling parameters, respectively, along the first transverse direction T1 and the second transverse direction T2. The decomposition of the affine DTI transformation matrix (as expressed by equation (1)) into matrices that describe rotation, shear, scaling and shift may be illustrated in equation (2) below.

$$\text{Affine (shift excluded)} = \begin{bmatrix} \cos(\theta) & -\sin(\theta) \\ \sin(\theta) & \cos(\theta) \end{bmatrix} \begin{bmatrix} 1 & Shx \\ Shy & 1 \end{bmatrix} \begin{bmatrix} Cx & 0 \\ 0 & Cy \end{bmatrix}. \quad \text{(eq. 2)}$$

Advancing to block 418 of FIG. 5, the controller C is programmed to calculate the transformation parameters from the matrices in the cascaded image registration process. Since the transformation matrix from the coarse registration stage may be regarded as a subset of an affine matrix, the results of the combined two-step registrations may be generalized as a single affine matrix if the two steps share the same transformation center 556 (see FIG. 7B).

Figure 6:
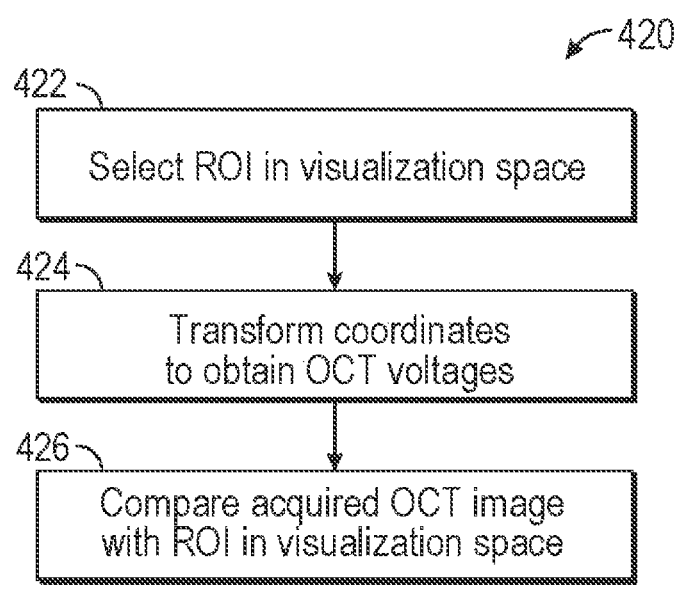
FIG. 6 is a flowchart of a portion of the method of FIG. 5.

Advancing to block 420 of FIG. 5, the method 400 may optionally include execution of a validation procedure, shown in detail in FIG. 6. Referring to FIG. 6, block 420 may include sub-modules 422, 424 and 426. Per sub-module 422 of FIG. 6, the method 400 includes selecting a region of interest (ROI) in the respective space (e.g., camera space) of the visualization module 12. In one embodiment, the region of interest is a line in visualization space that corresponds to a cross-sectional B-frame in OCT space.

Surgeons may draw (and move or rotate) certain lines of locations of interest on a camera image during or before surgery, to obtain correlated depth information through the OCT module 14. In the example shown in FIG. 8, the region of interest 670 in the eye 600 is a line indicating a region of iridocorneal angle that is useful for the diagnosis of glaucoma.

In another embodiment, the region of interest may be a quadrilateral (e.g., square) in visualization space that corresponds to a 3D volume in OCT space. Using the transformation parameters obtained in block 418, the validation procedure may correct the mismatches through coordinate transformation and generate a new scanning pattern (i.e., a list of voltages for the scanners), which may follow the equation below.

$$\text{Voltage} = \text{Affine}^{-1}[\text{ImageCoordinates} - \text{Trans}_{\text{Affine}} - \text{Center}_{\text{Affine}}] + [\text{Center}_{\text{Affine}} - \text{Trans}_{\text{Translation}}]$$

Figure 9:
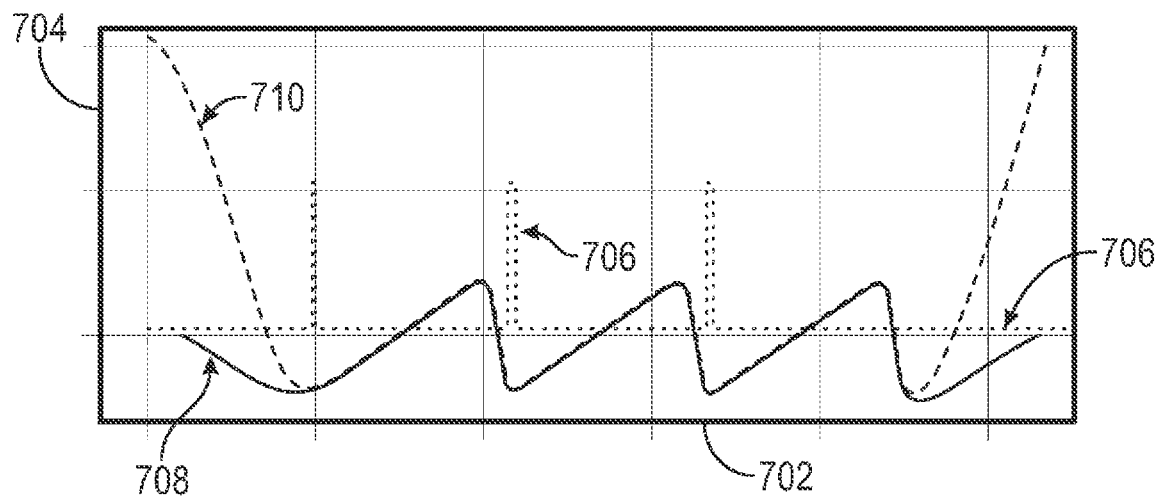
FIG. 9 is an example graph of a calibrated scanning pattern obtained by the method of FIG. 5.

FIG. 9 is an example graph of a calibrated scanning pattern obtained by the method 400 of FIG. 5. Referring to FIG. 9, the horizontal axis 702 indicates time while the vertical axis 704 indicates amplitude. Trace 706 indicates the B-frame trigger signal having a flat line punctuated by regular spikes. Trace 708 and trace 710 indicate the corresponding patterns of the X-Y Galvo scanners or voltage conversion factors for the X-axis and the Y-axis, respectively. Per sub-module 424 of FIG. 5, the controller C is programmed to transform the coordinates to obtain voltages that are sent out to the control scanners (e.g., two-dimensional scanner 122 in FIG. 2) while an OCT controller (e.g., OCT engine 126 in FIG. 2) acquires data synchronously to generate an acquired OCT image. In other words, the location of the region of interest 670 (corresponding to line 570 in the captured image 550 of FIG. 7B) may be converted to a new calibrated line of Galvo voltages in OCT coordinate space.

Proceeding to sub-module 426 of FIG. 6, the controller C is programmed to compare the acquired OCT image with the region of interest 670 in visualization space. The OCT data before and after calibration may be displayed side by side for validation and comparison. In one embodiment, this validation may be achieved through a direct usage of the calibration parameters in a real-time data acquisition. In another embodiment, this validation may be achieved through slicing/resampling of readily acquired OCT volume data. Evaluation of the image matching may be done using various methods available to those skilled in the art, such as dice coefficients. For example, an evaluation score of 532 with a dice coefficient of 0.96 may indicate a successful calibration compared to a low similarity of 0.08 before calibration (confidence level 80%).

In certain embodiments, the operations of loading the camera image, delineating the region of calibration, loading the OCT image, automatic image resizing, registration, and evaluation may be simplified as a click of one button. Depending on the size of the data, the OCT data acquisition and projection onto the en face plane may take several seconds to several minutes. The calibration process (e.g., pattern generation, image resizing, image registration, and coordinate transformation) may take several seconds. If the optical alignment of the visualization module 12 and the OCT module 14 are above a predefined threshold, a semi-automatic pre-alignment proves may be performed to achieve a more robust calibration. For example, a pre-alignment step may involve using respective mouse-clicks on the camera image and on the OCT projection image to restrict the registration boundaries. Depending on the environmental conditions in the operating room, frequency of the instrument usage, and stability of the visualization module 12 and/or surgical environment, the calibration frequency may range from a one-time manufacturing step to a daily routine procedure.

The controller C of FIG. 1 may include, or otherwise have access to, information downloaded from remote sources and/or executable programs. Referring to FIG. 1, the controller C may be configured to communicate with a remote server 60 and/or a cloud unit 62, via a network 64. The remote server 60 may be a private or public source of information maintained by an organization, such as for example, a research institute, a company, a university and/or a hospital. The cloud unit 62 may include one or more servers hosted on the Internet to store, manage, and process data.

The network 64 may be a serial communication bus in the form of a local area network. The local area network may include, but is not limited to, a Controller Area Network (CAN), a Controller Area Network with Flexible Data Rate (CAN-FD), Ethernet, blue tooth, WIFI and other forms of data. The network 64 may be a Wireless Local Area Network (LAN) which links multiple devices using a wireless distribution method, a Wireless Metropolitan Area Network (MAN) which connects several wireless LANs or a Wireless Wide Area Network (WAN) which covers large areas such as neighboring towns and cities. Other types of connections may be employed.

In summary, the system 10 enables automatic calibration of optical coherence tomography (OCT) systems to other imaging modalities, such as microscope camera imaging, thereby providing accurate 3D visualization during surgery. The system 10 utilizes a cascaded intensity-based image registration process to achieve fully automatic OCT calibration. The controller C is adapted to obtain respective transformation parameters, including rotation, shear, scaling, and shift parameters. An affine diffusion tensor transformation is utilized to generalize the transformation relation between OCT space and visualization space. The affine matrix may be further decoupled as matrices of rotation, shear, scaling and shift for further evaluation of each type of mismatch. The system 10 minimizes redundant human involvement and improves efficiency and repeatability. In one embodiment, the system 10 is employed for the calibration of lateral scanning of paired XY Galvo set in point-scanning OCT systems. The OCT images may include A-scans, B cross-section scans and 3D volumetric scans.

The system 10 provides a technical advantage over other calibration methods that employ a feedback signal from an integrated position detector. The accuracy of the feedback signal is adversely affected by environmental conditions, such as temperature and humidity, noise from electromagnetic interference, and high-frequency (1-20 kHz) dither. Additionally, the feedback signal given by a position detector is generally an optical measurement where the signal fluctuation depends on the rotation angle of a motor-shaft-bonded element between an LED light source and a photodetector that casts a shadow onto the detector. Thus, the position detectors integrated in a Galvo scanner may evaluate the scanned angle but not for any mismatches in the imaging optics or environment, which would be accounted for by the system 10.

The controller C of FIG. 1 may be an integral portion of, or a separate module operatively connected to, other controllers integrated with the OCT module 14 and visualization module 12. The controller C includes a computer-readable medium (also referred to as a processor-readable medium), including a non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random-access memory (DRAM), which may constitute a main memory. Such instructions may be transmitted by one or more transmission media, including coaxial cables, copper wire and fiber optics, including the wires that comprise a system bus coupled to a processor of a computer. Some forms of computer-readable media include, for example, a floppy disk, a flexible disk, hard disk, magnetic tape, other magnetic media, a CD-ROM, DVD, other optical media, a RAM, a PROM, an EPROM, a FLASH-EEPROM, other memory chips or cartridges, or other media from which a computer can read.

Look-up tables, databases, data repositories or other data stores described herein may include various kinds of mechanisms for storing, accessing, and retrieving various kinds of data, including a hierarchical database, a set of files in a file storage system, an application database in a proprietary format, a relational database energy management system (RDBMS), etc. Each such data store may be included within a computing device employing a computer operating system such as one of those mentioned above and may be accessed via a network in one or more of a variety of manners. A file system may be accessible from a computer operating system and may include files stored in various formats. An RDBMS may employ the Structured Query Language (SQL) in addition to a language for creating, storing, editing, and executing stored procedures, such as the PL/SQL language mentioned above.

The flowchart shown in the FIGS. illustrates an architecture, functionality, and operation of possible implementations of systems, methods, and computer program products according to various embodiments of the present disclosure. In this regard, each block in the flowchart or block diagrams may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by specific purpose hardware-based systems that perform the specified functions or acts, or combinations of specific purpose hardware and computer instructions. These computer program instructions may also be stored in a computer-readable medium that can direct a controller or other programmable data processing apparatus to function in a particular manner, such that the instructions stored in the computer-readable medium produce an article of manufacture including instructions to implement the function/act specified in the flowchart and/or block diagram blocks.

The numerical values of parameters (e.g., of quantities or conditions) in this specification, including the appended claims, are to be understood as being modified in each respective instance by the term "about" whether or not "about" actually appears before the numerical value. "About" indicates that the stated numerical value allows some slight imprecision (with some approach to exactness in the value; about or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of each value and further divided ranges within the entire range. Each value within a range and the endpoints of a range are hereby disclosed as separate embodiments.

The detailed description and the drawings or FIGS. are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims. Furthermore, the embodiments shown in the drawings, or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims.

What is claimed is:

1. An imaging system comprising:
    a housing assembly having a head unit configured to be at least partially directed towards a target site;
    an optical coherence tomography (OCT) module and a visualization module located in the housing assembly and configured to respectively obtain OCT data and visualization data of the target site;
    a controller in communication with the OCT module and the visualization module, the controller having a processor and tangible, non-transitory memory on which instructions are recorded for a method of calibration;
    wherein the controller is configured to:
        generate a scanning pattern for a region of calibration selected in a calibration target in visualization space;
        synchronously acquire the OCT data of the region of calibration with the scanning pattern;
        obtain a projected two-dimensional OCT image of the region of calibration based on the OCT data, the projected two-dimensional OCT image being an inverse mean-intensity projection on an en face viewing plane;
        overlay the projected two-dimensional OCT image with a corresponding view extracted from the visualization data; and
        register the projected two-dimensional OCT image to the corresponding view, via a cascaded image registration process having a coarse registration stage and a fine registration stage.

2. The imaging system of claim 1, wherein the visualization module is a stereoscopic camera, the visualization data including first and second views of the target site.

3. The imaging system of claim 1, wherein the visualization module is a surgical microscope.

4. The imaging system of claim 1, wherein the scanning pattern is an orthogonal raster scanning pattern.

5. The imaging system of claim 1, wherein the target site is an eye.

6. The imaging system of claim 1, wherein prior to registering the projected two-dimensional OCT image with the corresponding view extracted from the visualization data, the controller is configured to perform automatic image resizing.

7. The imaging system of claim 1, wherein the controller is adapted to calculate respective transformation parameters in the coarse registration stage based on a translation transformation matrix that compensates for mismatches in shift.

8. The imaging system of claim 1, wherein:
    the controller is adapted to calculate respective transformation parameters in the fine registration stage based on an affine diffusion tensor image (DTI) registration; and
    the respective transformation parameters are based in part on a rotation matrix, a shear matrix and a scaling matrix.

9. The imaging system of claim 8, wherein the controller is adapted to compensate for relatively small mismatches in shift introduced during operation of at least one of rotation, shear and scaling alignment.

10. The imaging system of claim 8, wherein the rotation matrix is expressed as $$\begin{bmatrix} \cos(\theta) & -\sin(\theta) \\ \sin(\theta) & \cos(\theta) \end{bmatrix},$$

where $\theta$ is the respective transformation parameter for rotation.

11. The imaging system of claim 8, wherein the shear matrix is expressed as $$\begin{bmatrix} 1 & Shx \\ Shy & 1 \end{bmatrix},$$

where Shx and Shy are shear parameters along a first transverse direction and a second transverse direction.

12. The imaging system of claim 8, wherein the scaling matrix is expressed as $$\begin{bmatrix} Cx & 0 \\ 0 & Cy \end{bmatrix},$$

where Cx and Cy are scaling parameters along a first transverse direction and a second transverse direction.

13. The imaging system of claim 1, wherein the controller is adapted to selectively execute a validation procedure, the controller being adapted to:
- select a region of interest in the visualization space;
- obtain respective voltages for OCT scanning based in part on the region of interest and respective transformation parameters;
- obtain acquired OCT image based on the respective voltages; and
- compare the acquired OCT image with the region of interest.

14. The imaging system of claim 13, wherein the region of interest is a line in the visualization space that corresponds to a cross-sectional B-frame in OCT space.

15. The imaging system of claim 13, wherein the region of interest is a quadrilateral in the visualization space that corresponds to a three-dimensional volume in OCT space.

16. The imaging system of claim 1, further comprising:
- a robotic arm operatively connected to and configured to selectively move the head unit; and
- wherein the robotic arm is selectively operable to extend a viewing range of the OCT module in three dimensions.

17. An imaging system comprising:
- a housing assembly having a head unit configured to be at least partially directed towards a target site;
- an optical coherence tomography (OCT) module and a visualization module located in the housing assembly and configured to respectively obtain OCT data and visualization data of the target site;
- a controller in communication with the OCT module and the visualization module, the controller having a processor and tangible, non-transitory memory on which instructions are recorded for a method of calibration;
- wherein the controller is configured to:
  - generate a scanning pattern for a region of calibration selected in a calibration target in visualization space;
  - synchronously acquire the OCT data of the region of calibration with the scanning pattern;
  - obtain a projected two-dimensional OCT image of the region of calibration based on the OCT data, the projected two-dimensional OCT image being an inverse mean-intensity projection on an en face viewing plane;
  - overlay the projected two-dimensional OCT image with a corresponding view extracted from the visualization data;
  - register the projected two-dimensional OCT image to the corresponding view, via a cascaded image registration process having a coarse registration stage and a fine registration stage; and
  - calculate respective transformation parameters in the fine registration stage based on an affine diffusion tensor image (DTI) registration.

18. The imaging system of claim 17, wherein the controller is adapted to calculate respective transformation parameters in the coarse registration stage based on a translation transformation matrix that compensates for mismatches in shift.

19. The imaging system of claim 18, wherein the controller is adapted to selectively execute a validation procedure, the controller being adapted to:
- select a region of interest in the visualization space;
- obtain respective voltages for OCT scanning based in part on the region of interest and the respective transformation parameters;
- obtain acquired OCT image based on the respective voltages; and
- compare the acquired OCT image with the region of interest.

* * * * *